United States Patent [19]

Angerbauer et al.

[11] Patent Number: 4,754,031
[45] Date of Patent: Jun. 28, 1988

[54] PREPARATION OF CEPHALOSPORINS

[75] Inventors: Rolf Angerbauer; Günther Kinast, both of Wuppertal, Fed. Rep. of Germany

[73] Assignee: Bayer Aktiengesellschaft, Leverkusen, Fed. Rep. of Germany

[21] Appl. No.: 731,248

[22] Filed: May 6, 1985

[30] Foreign Application Priority Data

May 22, 1984 [DE] Fed. Rep. of Germany ....... 3419015

[51] Int. Cl.⁴ ................. C07D 501/22; A61K 31/545
[52] U.S. Cl. .................... 540/225; 540/222
[58] Field of Search ............................ 544/25, 26, 27; 540/225, 222; 514/202, 203

[56] References Cited

U.S. PATENT DOCUMENTS 4,500,716  2/1985  Kinast .................... 544/27

FOREIGN PATENT DOCUMENTS 0023453  2/1981  European Pat. Off. .

Primary Examiner—Nicholas S. Rizzo
Attorney, Agent, or Firm—Sprung Horn Kramer & Woods

[57] ABSTRACT

A process for the preparation of a cephalosporin of the formula

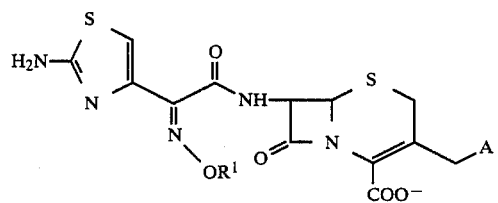

in which $R^1$ is an aliphatic or cycloaliphatic radical with up to 6 carbon atoms, and A is a pyridinium radical or a radical of the formula

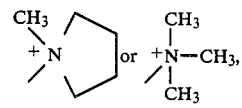

comprising reacting an acid of the formula

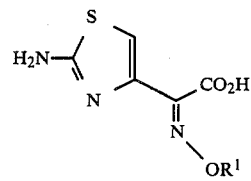

with methanesulphonyl chloride to form an anhydride of the formula

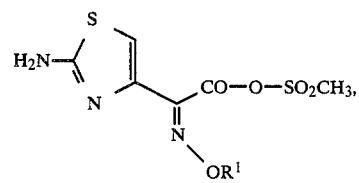

and reacting the anhydride with a 7-aminocephalosporanate of the formula

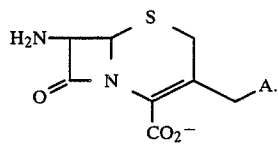

The reaction proceeds smoothly and in high yield.

11 Claims, No Drawings

PREPARATION OF CEPHALOSPORINS

The invention relates to a process for the preparation of known cephalosporins of the general formula I

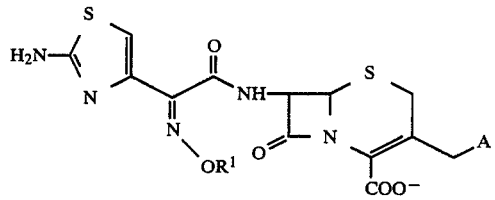

which are mentioned in, inter alia, European Pat. No. 64,740, European Pat. No. 74,645, DE-OS (German Published Specification) No. 3,311,300 and U.S. Pat. No. 4,406,899, and in which $R^1$ represents a $C_1$-$C_6$-alkyl radical which can be straight-chain, branched, cyclic as well as unsaturated, and A denotes a pyridinium radical

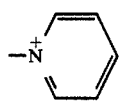

which can be substituted one or several times, or represents a radical of the formula

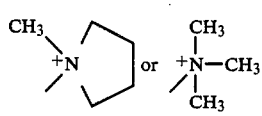

The process is characterized in that an acid of the general formula II is converted, with methanesulphonyl chloride, into the desired anhydride III, and the latter is reacted with a 7-aminocephalosporanate of the general formula IV in which A has the abovementioned meaning.

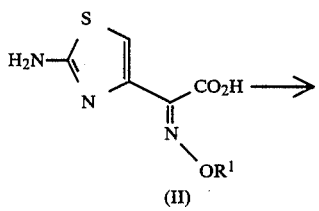

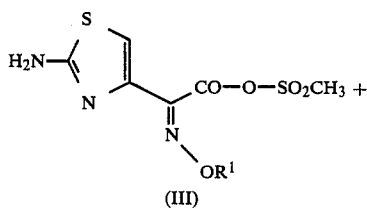

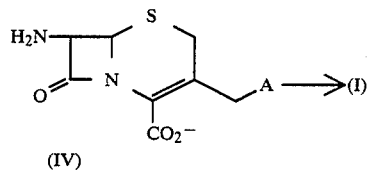

The mixed anhydrides are prepared by dissolving the carboxylic acid of the formula II and 1-1.1 equivalent of an amine in a solvent, and allowing them to react with 1-1.2 equivalents of methanesulphonyl chloride.

Suitable solvents are all solvents which are stable under the reaction conditions, such as, for example, diethyl ether, tetrahydrofuran, acetonitrile, acetone, methylene chloride, chloroform, dimethylformamide or mixtures of these.

Suitable amines are tertiary amines, such as, for example, triethylamine, tripropylamine, tributylamine, ethyldiisopropylamine, sterically hindered secondary amines, such as, for example, diisopropylamine, or mixtures of these amines.

The reaction temperature can be between $-80°$ C. and room temperature, low temperatures being a particular advantage when dimethylformamide is used.

For the subsequent reaction of the mixed anhydride III with 7-aminocephalosporanates IV, it is advantageous, for reasons of solubility, to prepare the anhydrides III in dimethylformamide at $-40°$ to $-60°$ C. with a reaction lasting from 0.2 to 24 h, preferably 0.5-2 h, and to react the resulting solution of the mixed anhydride III directly with a solution of 0.5-2.0 equivalents of the 7-aminocephalosporanates IV in a suitable solvent and a suitable base to give the desired products I.

For the abovementioned reaction of II and IV to give I, for reasons of solubility the 7-aminocephalosporanates IV are dissolved in a polar solvent, dimethylformamide, dimethyl sulphoxide, diglyme or water, preferably in water. The solutions of III and of IV and the base are mixed at a suitable temperature and vigorously stirred until the reaction is complete.

The base which is used can be the abovementioned tertiary and sterically hindered secondary amines, of which 1-2.5 equivalents, based on the anhydride III, are used. Triethylamine is preferably used. However, it is also possible to use as the base inorganic bases, such as NaOH, KOH, $NaHCO_3$ or $K_2CO_3$ and their aqueous solutions. During the reaction, the pH should be above 7 and may, depending on the stability of the final product I, briefly reach as far as 12. Higher pH values increase the reaction rate.

The reaction temperature is between $-50°$ C. and $+50°$ C., reaction temperatures below 0° C. being preferred for reactions at pH values above 9.

The reaction time depends on the reaction temperature and the pH and is between a few minutes and several hours. In general, the reaction is complete after 5 to 20 minutes at temperatures from $-20°$ to 0° C. and at a pH of about 9.

The working up depends on the properties of the starting compounds II and IV, of the amine used and of the bases and on the properties of the products I. In general, it is possible to precipitate out or crystallize out of the reaction solution the products I after addition of an acid and the corresponding salts of the products I using a suitable solvent, such as, for example, acetone, ethanol or isopropanol.

Compounds of the formula I in which R¹ represents a methyl group and A represents a radical of the formula

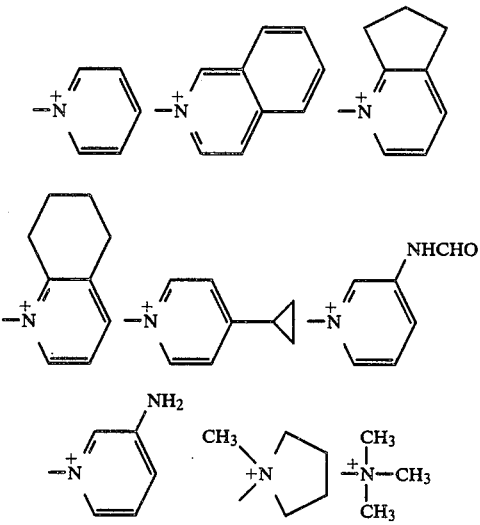

are particularly preferably prepared by the process according to the invention.

The described process for the preparation of the compounds of the formula I has the advantage that
1. the amino group in II need not be protected
2. the N"OR¹ group with the Z configuration does not isomerize to the undesired E configuration
3. the reagent used for activation of the carboxylic acids II, methanesulphonyl chloride, is reasonably priced and easy to handle
4. the reaction of III with IV is easily controlled by varying the reaction conditions
5. and can also be carried out in aqueous systems, which is particularly advantageous for reasons of the solubility of compound IV
6. the removal of the methanesulphonic acid which is produced in the reaction of III with IV entails no problems
7. the reaction yields of the desired product I are very high.

EXAMPLE 1

7β-[(Z)-2-(2-Aminothiazol-4-yl)-2-methoxyiminoacetamido]-3-pyridiniummethyl-3-cephem-4-carboxylate 37.66 g (0.187 mol) of 2-aminothiazol-4-ylmethoxyiminoacetic acid and 34.2 ml (0.196 mol) of ethyldiisopropylamine are dissolved in 160 ml of dimethylformamide, the solution is cooled to −60° C., and 15.1 ml (0.196 mol) of methanesulphonyl chloride are added. The solution is stirred at −60° to −50° C. for 40 min and poured all at once into a solution, precooled to 0° C., of 50 g (0.149 mol) of 7-amino-2-pyridiniummethyl-2-cephem-3-carboxylate×1 HCl×1 H₂O and 55 ml (0.40 mol) of triethylamine in 54 ml of water and stirred very vigorously, without cooling, for 10 minutes. The mixture is then introduced into 7.5 liters of acetone, and the precipitate is filtered off with suction, washed with acetone and methylene chloride and dried. 66 g (96%) of the desired product are obtained, and this can be converted into a crystalline dihydrochloride by dissolving in 64 ml of concentrated hydrochloric acid and addition of 64 ml of 2N hydrochloric acid and 250 ml of isopropanol. Yield of dihydrochloride: 60 g (76%).

¹H-NMR (D₂O).

δ (ppm)=9.04 (2H, d, J=7 Hz, H-2,6-py); 8.68 (1H, m, H-4-py); 8.19 (2H, m, H-3,5-py); 7.18 (1H, s, thiazole); 5.93 (1H, d, J=5 Hz, H-7-lactam); 5.89 (1H, d, J=15 Hz, CH₂-py); 5.49 (1H, d, J=15 Hz, CH₂-Py); 5.39 (1H, d, J=5 Hz, H-6-lactam); 4.10 (3H, s, OCH₃); 3.82 (1H, d, J=18 Hz, S-CH₂); 3.43 (1H, d, J=18 Hz, S—CH₂).

EXAMPLE 2

7β-[(Z)-2-(2-Aminothiazol-4-yl)-2-methoxyiminoacetamido]-3-(1-methyl-1-pyrrolidinium)methyl-3-cephem-4-carboxylate 719 mg (3.58 mmol) of (Z)-2-(2-aminothiazol-4-yl)-2-methoxyiminoacetic acid are dissolved in 4.5 ml of absolute dimethylformamide under nitrogen at room temperature. After addition of 230 µl of N-ethyldiisopropylamine, 250 µl of tripropylamine and 310 µl of tributylamine, the mixture is cooled to −50° C. 290 µl of mesyl chloride are added, and the solution is stirred at −50° C. for 30 minutes. This solution is then rapidly added to a solution, cooled to 0° C., of 900 mg (2.6 mmol) of 7-amino-3-(1-methyl-1-pyrrolidinium)methyl-3-cephem-4-carboxylate (×HCl) in 1.4 ml of water and 1.4 ml of triethylamine. After 5 minutes, the reaction solution is poured into 400 ml of acetone. The precipitate is filtered off with suction, dried and chromatographed on adsorber resin HP 20 (mobile phase: acetonitrile/water 5/95).

Yield: 909 mg (63%).

¹H-NMR (DMSO-d₆).

δ (ppm)=9.61 (1H, d, J=9 Hz, NH); 7.27 (2H, s, NH₂); 6.74 (1H, s, aminothiazole); 5.65 (1H, dd, J=9 Hz, J=5 Hz, H-7); 5.13 (1H, d, J=5 Hz, H-6); 5.02 (1H, d, J=13 Hz, CH₂-pyrrol.); 3.91 (1H, d, J=13 Hz, CH₂-pyrrol.); 3.84 (3H, s, OCH₃); 3.82 (1H, d, J=18 Hz, S—CH₂); 3.44 (4H, m, pyrrol.); 3.32 (1H, d, J=18 Hz, S—CH₂); 2.92 (3H, s, CH₃±N—); 2.08 (4H, m, pyrrol.).

EXAMPLE 3

7β-[(Z)-2-(2-Aminothiazol-4-yl)-2-methoxyiminoacetamido]-3-(trimethylammonium)methyl-3-cephem-4-carboxylate The preparation is carried out in analogy to Example 2, from (Z)-2-(2-aminothiazol-4-yl)-2-methoxyiminoacetic acid and 7-amino-3-(trimethylammonium)methyl-3-cephem-4-carboxylate.

¹H-NMR (DMSO-d₆).

δ (ppm)=9.62 (1H, d, J=9 Hz, NH); 7.27 (2H, bs, NH₂): 6.75 (1H, s, thiazole); 6.66 (1H, dd, J=9 Hz, J=5 Hz, H-7-lactam); 5.16 (1H, d, J=5 Hz, H-6-lactam); 5.01 (1H, d, J=14 Hz, CH₂-ammon.); 3.91 (1H, d, J=14 Hz, CH₂-ammon.); 3.84 (3H, s, OCH₃); 3.83 (1H, d, J=18 Hz, S—CH₂); 3.29 (1H, d, J=18 Hz, S—CH₂); 3.00 (9H, s, ±

).

EXAMPLE 4

7β-[(Z)-2-(2-Aminothiazol-4-yl)-2-methoxyiminoacetamido]-3-(4-cyclopropylpyridinium)methyl-3-cephem-4-carboxylate The preparation is carried out in analogy to Example 2, from (Z)-2-(2-aminothiazol-4-yl)-2-methoxyiminoacetic acid and 7-amino-3-(4-cyclopropylpyridinium)-methyl-3-cephem-4-carboxylate.

$^1$H-NMR (DMSO-$d_6$).

δ (ppm)=9.51 (1H, d, J=9, Hz, NH); 9.22 (2H, d, H=6 Hz, H-2,6-py); 8.81 (2H, d, J=6 Hz, H-3,5-py); 7.20 (2H, bs, NH$_2$); 6.68 (1H, s, thiazole); 5.62 (1H, dd, J=9 Hz, J=5 Hz, H-7-lactam); 5.53 (1H, d, J=13 Hz, CH$_2$-py); 5.03 (1H, d, J=5 Hz, H-6-lactam); 4.93 (1H, d, J=13 Hz, CH$_2$-py); 3.78 (3H, s, OCH$_3$); 3.49 (1H, d, J=18 Hz, S—CH$_2$); 2.98 (1H, cycloprop.); 1.37 (2H, m, cycloprop.); 1.11 (2H, m, cycloprop.).

EXAMPLE 5

7β-[(Z)-2-(2-Aminothiazol-4-yl)-2-methoxyiminoacetamido]-3-isoquinolinium-3-cephem-4-carboxylate The preparation is carried out in analogy to Example 2 from (Z)-2-(2-aminothiazol-4-yl)-2-methoxyiminoacetic acid and 7-amino-3-isoquinolinium-3-cephem-4-carboxylate.

$^1$H-NMR (DMSO-$d_6$).

δ (ppm)=10.24 (1H, s, H-1-isoquin.); 9.51 (1H, d, J=9 Hz, NH); 9.42 (1H, d, J=8 Hz, H-3-isoquin.); 8.59 (1H, d, J=7 Hz, isoquin.); 8.48 (1H, d, J=8 HZ, isoquin.); 8.30 (1H, m, isoquin.); 8.25 (1H, m, isoquin.); 8.06 (1H, m, isoquin.); 7.19 (2H, bs, NH$_2$); 6.68 (1H, s. thiazole); 5.72 (1H, d, J=14 Hz, CH$_2$-isoquin.); 5.65 (1H, dd, J=9 Hz, J=5 Hz, H-7-lactam); 5.21 (1H, d, J=14 Hz, CH$_2$-isoquin.); 5.06 (1H, d, J=5 Hz, H-6-lactam); 3.76 (3H, s, OCH$_3$); 3.53 (1H, d, J=18 Hz, S—CH$_2$); 3.16 (1H, d, J=18 Hz, S—CH$_2$).

EXAMPLE 6

7β-[(Z)-2-(2-Aminothiazol-4-yl)-2-methoxyiminoacetamido]-3-(2,3-cyclopentenopyridinium)-methyl-3-cephem-4-carboxylate The preparation is carried out in analogy to Example 2, from (Z)-2-(2-aminothiazol-4-yl)-2-methoxyiminoacetic acid and 7-amino-3-(2,3-cyclopentenopyridinium)-methyl-3-cephem-4-carboxylate.

$^1$H-NMR (DMSO-$d_6$).

δ (ppm)=9.57 (1H, d, J=8 Hz, H-6-py); 9.29 (1H, d, J=7 Hz, NH); 8.37 (1H, d, J=8 Hz, H-4-py); 7.91 (1H, m, H-5-py); 7.24 (2H, bs, NH$_2$); 6.71 (1H, s, thiazole); 5.65 (1H, dd, J=7 Hz, J=5 Hz, H-7-lactam); 5.47 (1H, d, J=14 Hz, CH$_2$-py); 5.22 (1H, d, J=14 Hz, CH$_2$-py); 5.05 (1H, d, J=5 Hz, H-6-lactam); 3.80 (2H, s, OCH$_3$); 3.40 (1H, d, J=18 Hz, S—CH$_2$); 3.39 (2H, m, py-CH$_2$); 3.12 (3 H, m, py-CH$_2$, S—CH$_2$); 2.21 (1H, m, —CH$_2$—).

EXAMPLE 7

7β-[(Z)-2-(2-Aminothiazol-4-yl)-2-methoxyiminoacetamido]-3-(5,6,7,8-tetrahydroquinolinium)-methyl-3-cephem-4-carboxylate The preparation is carried out in analogy to Example 2 from (Z)-2-(2-aminothiazol-4-yl)-2-methoxyiminoacetic acid and 7-amino-3-(5,6,7,8-tetrahydroquinolinium)methyl-3-cephem-4-carboxylate.

$^1$H-NMR (DMSO-$d_6$).

δ (ppm)=9.63 (1H, d, J=9 Hz, NH); 9.28 (1H, d, J=7 Hz, H-6-py); 8.32 (1H, d, J=8 Hz, H-4-py); 7.64 (1H, m, H-5-py); 7.31 (2H, bs, NH$_2$); 6.75 (1H, s, thiazole); 5.69 (1H, dd, J=9 Hz, J=5 Hz, H-7-lactam); 5.48 (1H, d, J=14 Hz, CH$_2$-py); 5.36 (1H, d, J=14 Hz, CH$_2$-py); 5.09 (1H, d, J=5 Hz, H-6-lactam); 3.83 (3H, s, OCH$_3$); 3.42 (1H, d, J=18 Hz, S—CH$_2$); 3.17 (2H, m, py-CH$_2$); 3.14 (1H, d, J=18 Hz, S—CH$_2$); 2.97 (2H, m, py-CH$_2$); 1.91 (2H, m, —CH$_2$—); 1.79 (2H, m, —CH$_2$—).

EXAMPLE 8

7β-[(Z)-2-(2-aminothiazol-4-yl)-2-methoxyiminoacetamido]-3-(3-formamidopyridinium)methyl-3-cephem-4-carboxylate The preparation is carried out in analogy to Example 2, from (Z)-2-(2-aminothiazol-4-yl)-2-methoxyiminoacetic acid and 7-amino-3-(3-formamidopyridinium)-methyl-3-cephem-4-carboxylate.

$^1$H-NMR (DMSO-$d_6$).

δ (ppm)=9.67 (1H, s, H-2-py); 9.58 (1H, d, J=9 Hz, NH); 9.24 (1H, d, J=7 Hz, H-6-py); 8.74 1H, d, J=8 Hz, H-4-py); 8.54 (1H, s, CHO); 8.13 (1H, m, H-5-py); 7.24 (2H, bs, NH$_2$); 6.72 (1H, s, thiazole); 5.73 (1H, d, J=14 Hz, CH$_2$-py); 5.68 (1H, dd, J=9, Hz, J=5 Hz, H-7-lactam); 5.24 (1H, d, J=14 Hz, CH$_2$-py); 5.09 (1H, d, J=5 Hz, H-6-lactam); 3.80 (3H, s, OCH$_3$); 3.55 (1H, d, J=18 Hz, S—CH$_2$); 3.15 (1H, d, J=18 Hz, S—CH$_2$).

EXAMPLE 9

7β-[(Z)-2-(2-Aminothiazol-4-yl)-2-methoxyiminoacetamido]-3-(3-aminopyridinium)methyl-3-cephem-4-carboxylate 520 mg (1 mmol) of 7β-[(Z)-2-(2-aminothiazol-4-yl)-2-methoxyiminoacetamido]-3-(3-formamidopyridinium)methyl-3-cephem-4-carboxylate are suspended in 6 ml of methanol and induced to dissolve by addition of 0.4 ml of concentrated hydrochloric acid. After 5 h, the methanol is removed in vacuo and the residue is taken up in 20 ml of water. The solution is neutralized with ion exchanger MP 62 and then freeze-dried.

Yield: 350 mg (71%).

$^1$H-NMR (DMSO-$d_6$).

δ (ppm)=9.51 (1H, d, J=9 Hz, NH); 8.52 (1H, s, H-2-py); 8.44 (1H, d, J=7 Hz, H-6-py); 7.71 (1H, dd, J=7 Hz, J=8 Hz, H-5-py); 7.63 (1H, d, J=8 Hz, H-4-py); 7.26 (2H, bs, NH$_2$); 6.83 (2H, bs, NH$_2$); 6.72 (1H, s, thiazole); 5.62 (1H, dd, J=9 Hz, J=5 Hz, H-7-lactam); 5.60 (1H, d, J=13 Hz, CH$_2$-py); 5.09 (1H, d, J=5 Hz); 5.08 (1H, d, J=13 Hz, CH$_2$-py); 3.81 (3H, s, OCH$_3$); 3.53 (1H, d, J=18 Hz, S—CH$_2$); 3.07 (1H, d, J=18 Hz, S—CH$_2$).

It is understood that the specification and examples are illustrative but not limitative of the present invention and that other embodiments within the spirit and scope of the invention will suggest themselves to those skilled in the art.

We claim:

1. A process for the preparation of a Z-cephalosporin of the formula

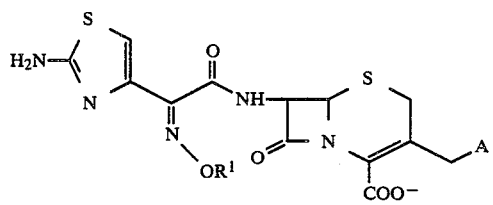

in which

R[1] is an aliphatic or cycloaliphatic radical with up to 6 carbon atoms, and

A is a pyridinium radical or a radical of the formula

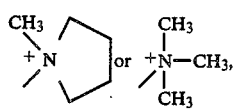

comprising reacting an acid of the formula

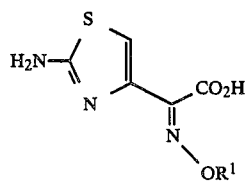

with methanesulphonyl chloride at a temperature $\leq 0°$ C. to form an anhydride of the formula

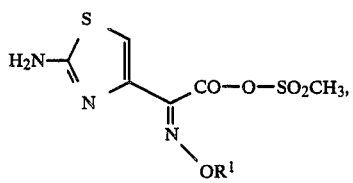

and reacting the anhydride with a 7-aminocephalosporanate of the formula

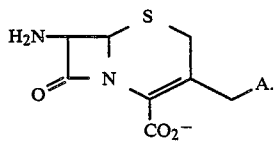

2. A process according to claim 1, in which R[1] is a methyl group, and A is a radical of the formula

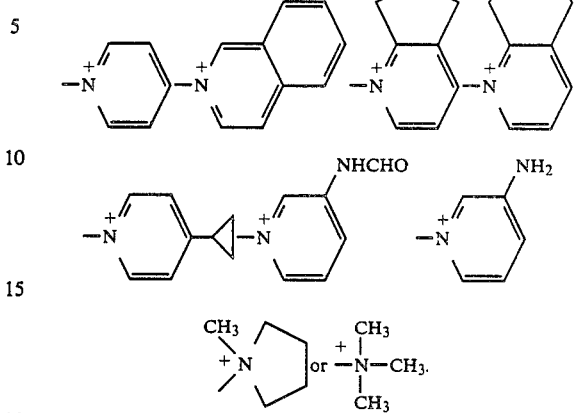

3. A process according to claim 1, wherein the anhydride is prepared by dissolving about 1 to 1.1 equivalents of an amine and of the carboxylic acid in a solvent and reacting the solution with about 1 to 1.2 equivalents of methanesulphonyl chloride.

4. A process according to claim 3, wherein the solvent is at least one of diethyl ether, tetrahydrofuran, acetonitrile, acetone, methylene chloride, chloroform and dimethylformamide.

5. A process according to claim 3, wherein the amine is at least one of triethylamine, tripropylamine, tributylamine, ethyldiisopropylamine and diisopropylamine.

6. A process according to claim 3, wherein the anhydride formation is carried out at a temperature between about $-80°$ C. and $0°$ C.

7. A process according to claim 1, wherein the reaction of the anhydride with a 7-aminocephalosporanate is carried out in dimethylformamide, dimethyl sulphoxide, diglyme or water in the presence of a base.

8. A process according to claim 7, wherein the reaction of the anhydride is carried out in the presence of triethylamine, NaOH, KOH, NaHCO$_3$ or K$_2$CO$_3$.

9. A process according to claim 7, wherein the reaction of the anhydride is carried out at $-50°$ C. to $0°$ C.

10. A process according to claim 7, wherein the reaction of the anhydride is carried out at a pH $\geq 9$.

11. A process according to claim 4, wherein the amine is at least one of triethylamine, tripropylamine, tributylamine, ethyldiisopropylamine and diisopropylamine, the anhydride formation is carried out at a temperature between about $-80°$ C. and room temperature, and the reaction of the anhydride with a 7-aminocephalosporanate is carried out in dimethylformamide, dimethyl sulphoxide, diglyme or water in the presence of triethylamine, NaOH, KOH, NaHCO$_3$ or K$_2$CO$_3$ at a pH$\leq 9$.

* * * * *